United States Patent
Biedermann et al.

(10) Patent No.: US 8,152,849 B2
(45) Date of Patent: Apr. 10, 2012

(54) IMPLANT WITH ONE PIECE SWIVEL JOINT

(75) Inventors: Lutz Biedermann, VS-Villingen (DE);
Wilfried Matthis, Weisweil (DE);
Jürgen Harms, VS-Schwenningen (DE)

(73) Assignee: Biedermann Motech GmbH & Co. KG, Villingen-Schwenningen (DE)

( * ) Notice: Subject to any disclaimer, the term of this patent is extended or adjusted under 35 U.S.C. 154(b) by 1036 days.

(21) Appl. No.: 11/588,687

(22) Filed: Oct. 26, 2006

(65) Prior Publication Data

US 2007/0093904 A1   Apr. 26, 2007

Related U.S. Application Data

(60) Provisional application No. 60/730,587, filed on Oct. 26, 2005.

(30) Foreign Application Priority Data

Oct. 26, 2005   (EP) .................................... 05110043

(51) Int. Cl.
*A61F 2/44* (2006.01)
(52) U.S. Cl. ................................................... 623/17.15
(58) Field of Classification Search .... 623/17.11–17.16; 606/254–263; 403/310–313
See application file for complete search history.

(56) References Cited

U.S. PATENT DOCUMENTS

| | | | | |
|---|---|---|---|---|
| 5,299,980 A | * | 4/1994 | Agius | 464/99 |
| 5,320,644 A | * | 6/1994 | Baumgartner | 623/17.16 |
| 5,458,638 A | * | 10/1995 | Kuslich et al. | 623/17.11 |
| 6,136,031 A | * | 10/2000 | Middleton | 623/17.16 |
| 6,159,211 A | | 12/2000 | Boriani et al. | |
| 6,203,437 B1 | * | 3/2001 | Durie et al. | 464/78 |
| 6,395,035 B2 | * | 5/2002 | Bresina et al. | 623/17.15 |
| 6,579,321 B1 | | 6/2003 | Gordon et al. | |
| 7,097,564 B2 | * | 8/2006 | Berg | 464/78 |
| 7,179,295 B2 | * | 2/2007 | Kovacevic | 623/17.15 |
| 2001/0016774 A1 | * | 8/2001 | Bresina et al. | 623/17.15 |
| 2003/0009226 A1 | | 1/2003 | Graf | |
| 2004/0176172 A1 | * | 9/2004 | Berg | 464/78 |

(Continued)

FOREIGN PATENT DOCUMENTS

DE   4323034 C1   7/1994

(Continued)

OTHER PUBLICATIONS

European Search Report for European Application No. 05110043.6-2310 dated Nov. 9, 2006 and mailed Nov. 17, 2006, 15pp.

*Primary Examiner* — Eduardo C Robert
*Assistant Examiner* — Steven Cotroneo
(74) *Attorney, Agent, or Firm* — Christie, Parker & Hale, LLP

(57) ABSTRACT

An implant for permanent or temporary introduction into the human or animal body includes a base body for connecting spaced body parts and/or other implant components, the implant having a load axis, along which primarily tensile and/or compressive forces are transmissible, with at least one rotary axis formed at right angle to the load axis, the rotary axis facilitating at least limited bending of the base body about the rotary axis, especially of the ends of the base body arranged along the load axis, with the at least one rotary axis being defined by a swivel joint, which is formed in one-piece at the base body.

25 Claims, 11 Drawing Sheets

U.S. PATENT DOCUMENTS

| | | |
|---|---|---|
| 2005/0131405 A1 | 6/2005 | Molz, IV et al. |
| 2006/0241760 A1* | 10/2006 | Randall et al. ............. 623/17.11 |
| 2007/0123990 A1* | 5/2007 | Sharifi-Mehr ............. 623/17.16 |
| 2008/0004704 A1* | 1/2008 | Katz ......................... 623/17.16 |

FOREIGN PATENT DOCUMENTS

| | | |
|---|---|---|
| DE | 10337088 A1 | 3/2005 |
| EP | 0268115 B1 | 5/1988 |
| EP | 0538183 A1 | 4/1993 |
| EP | 0677277 A2 | 10/1995 |
| EP | 0716841 A1 | 6/1996 |
| EP | 0950389 A2 | 10/1999 |
| FR | 2775587 A1 | 9/1999 |
| WO | WO 01/39678 A1 | 6/2001 |
| WO | WO 01/93785 A2 | 12/2001 |
| WO | WO 01/93786 A2 | 12/2001 |
| WO | WO 2004/105577 A2 | 12/2004 |
| WO | WO 2005/039454 A2 | 5/2005 |

* cited by examiner

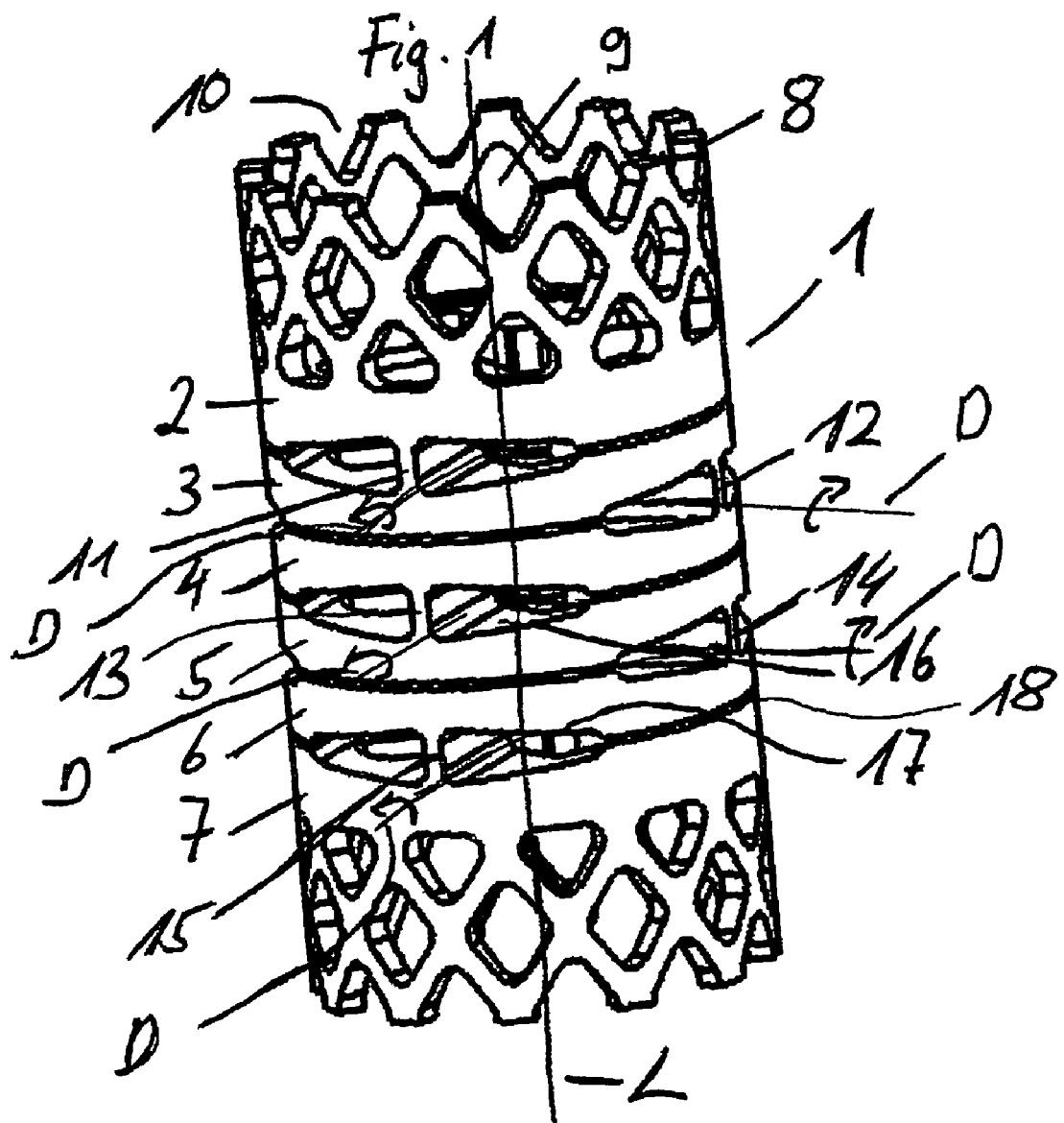

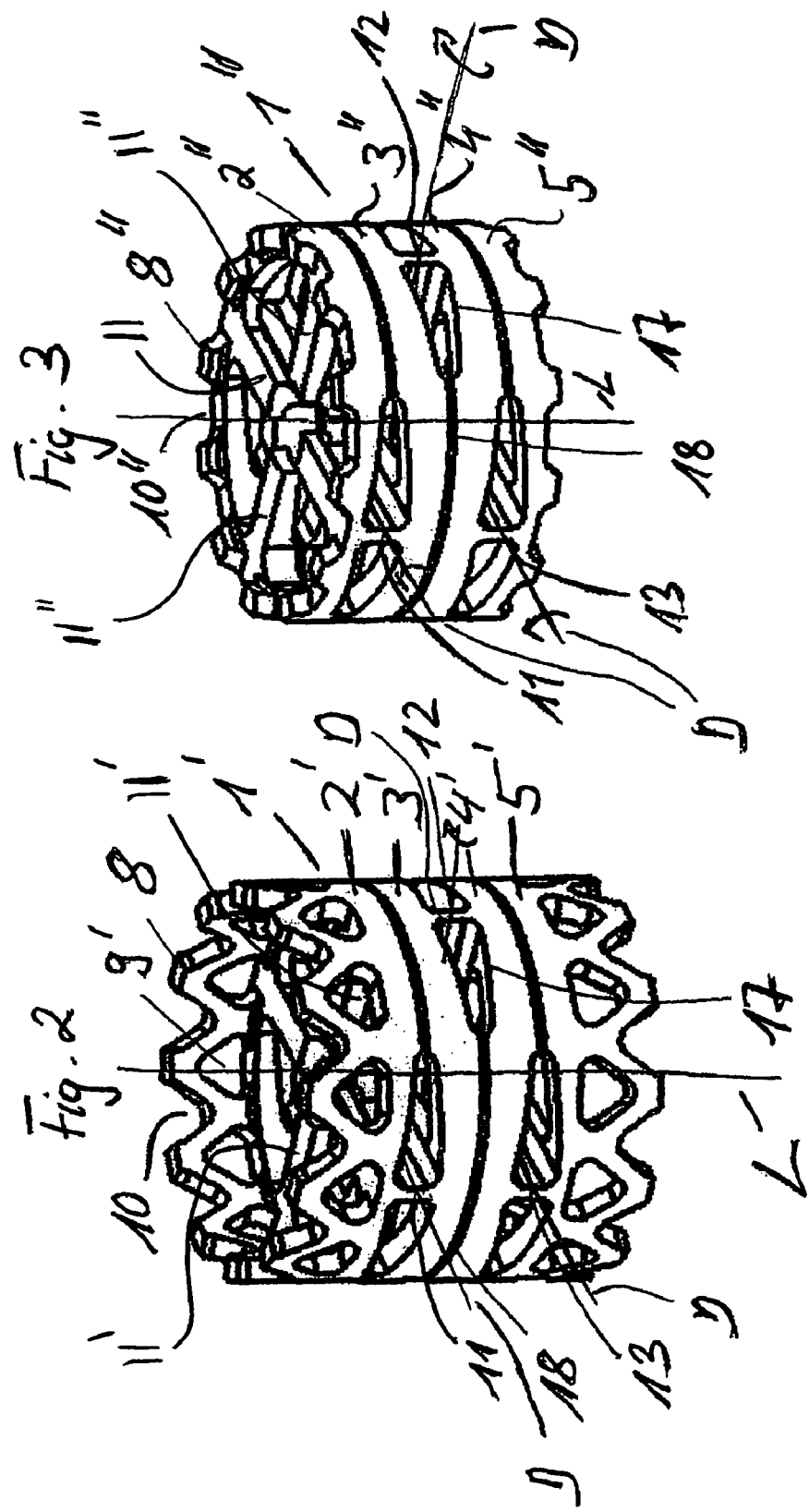

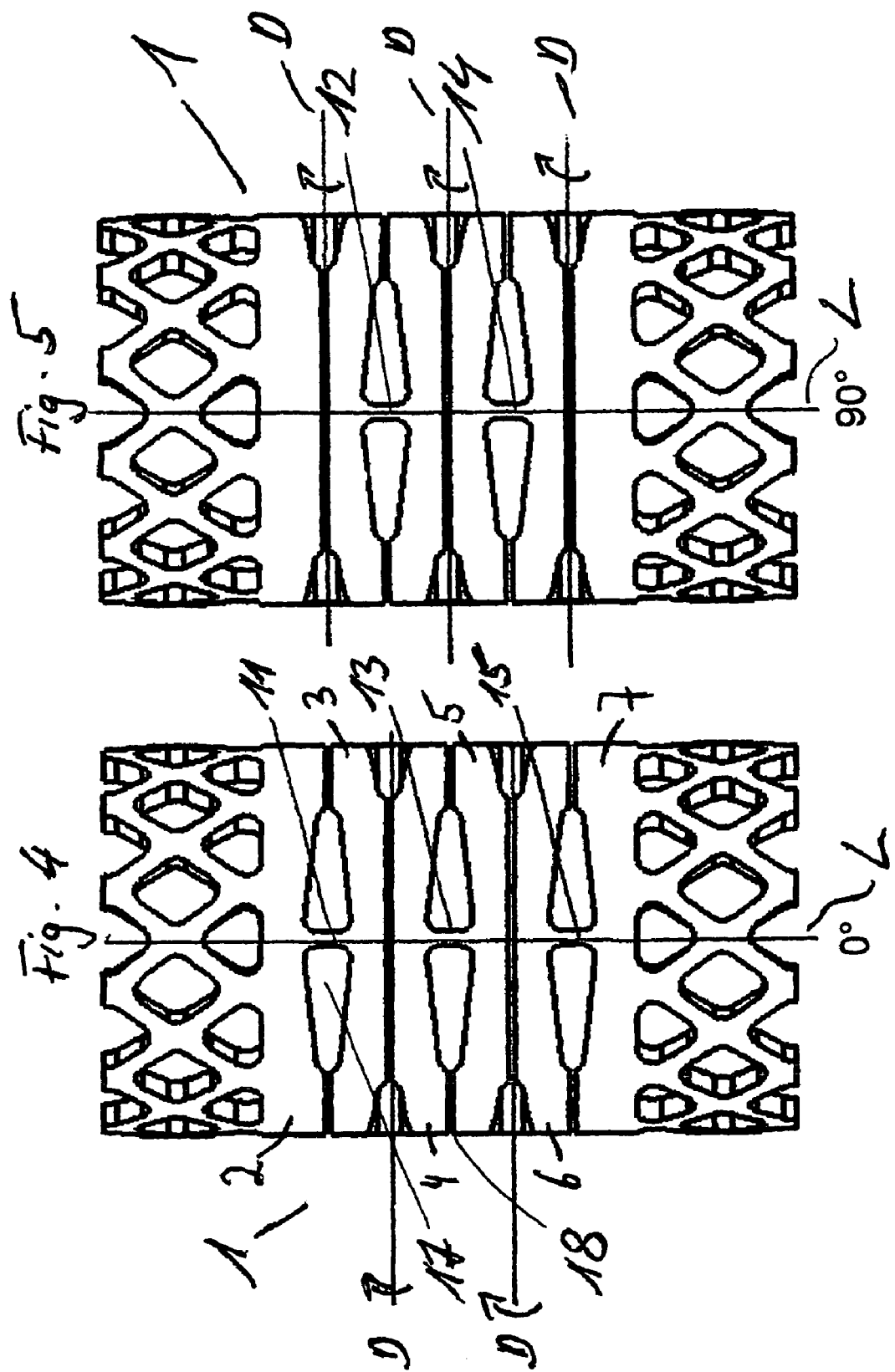

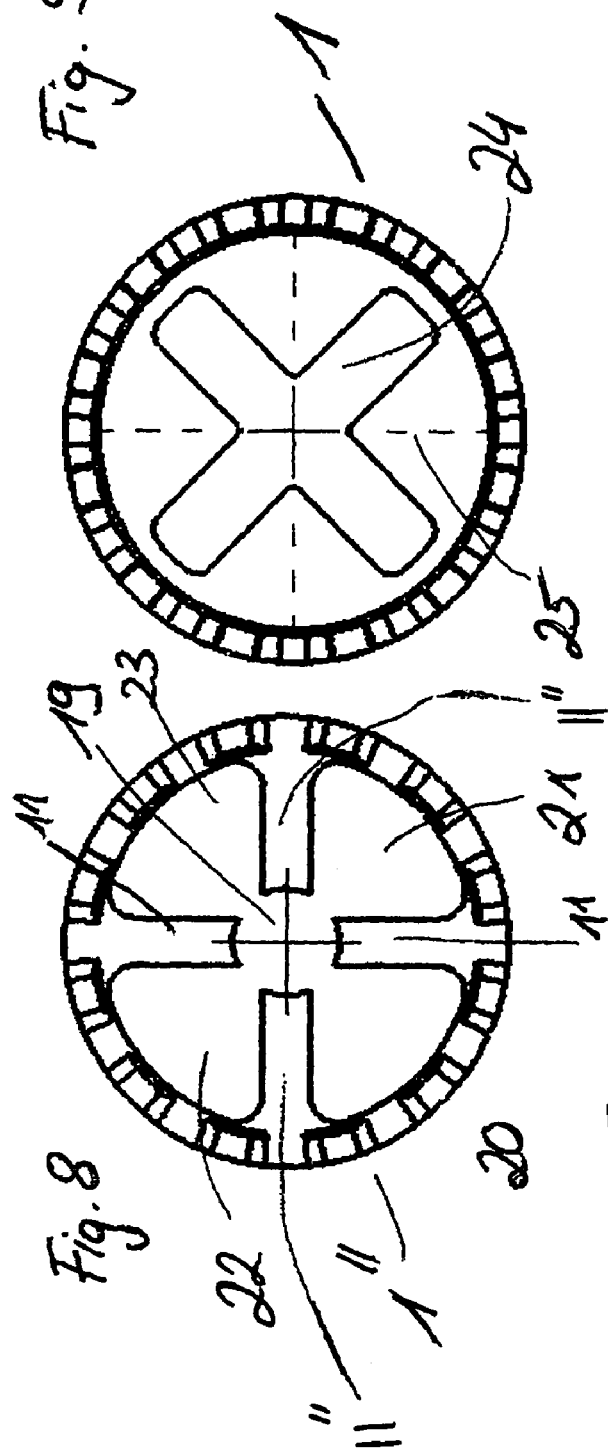

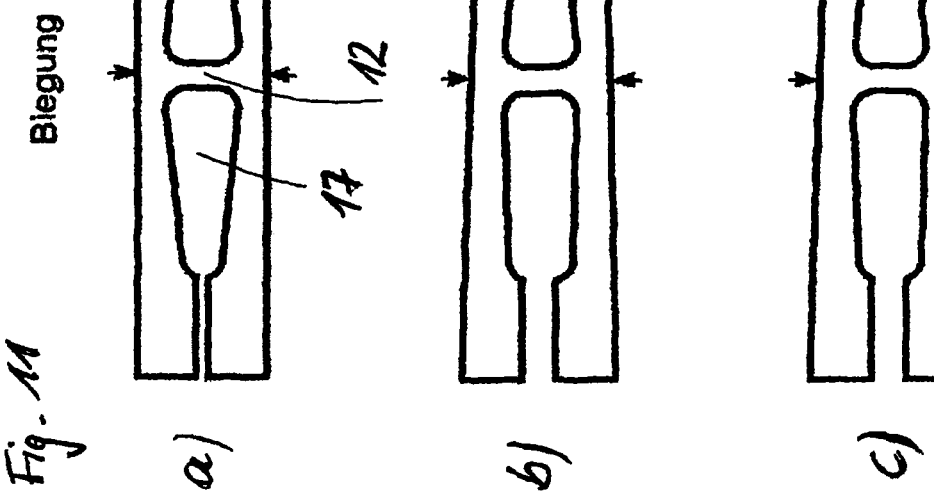
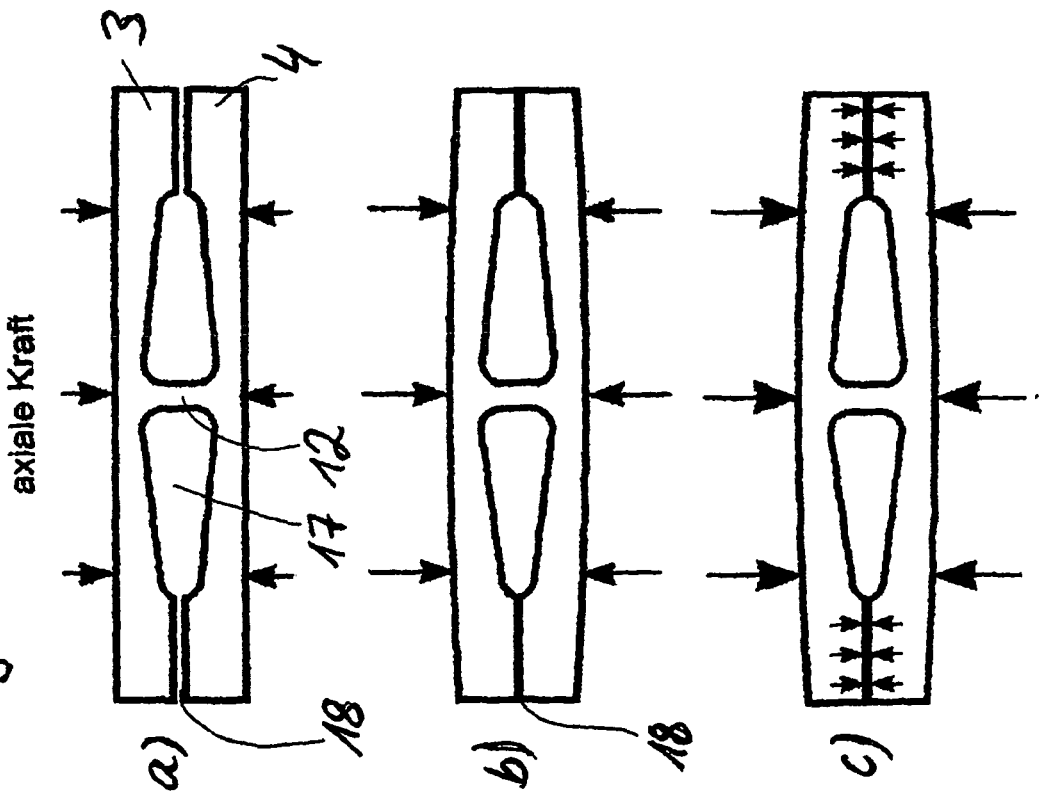

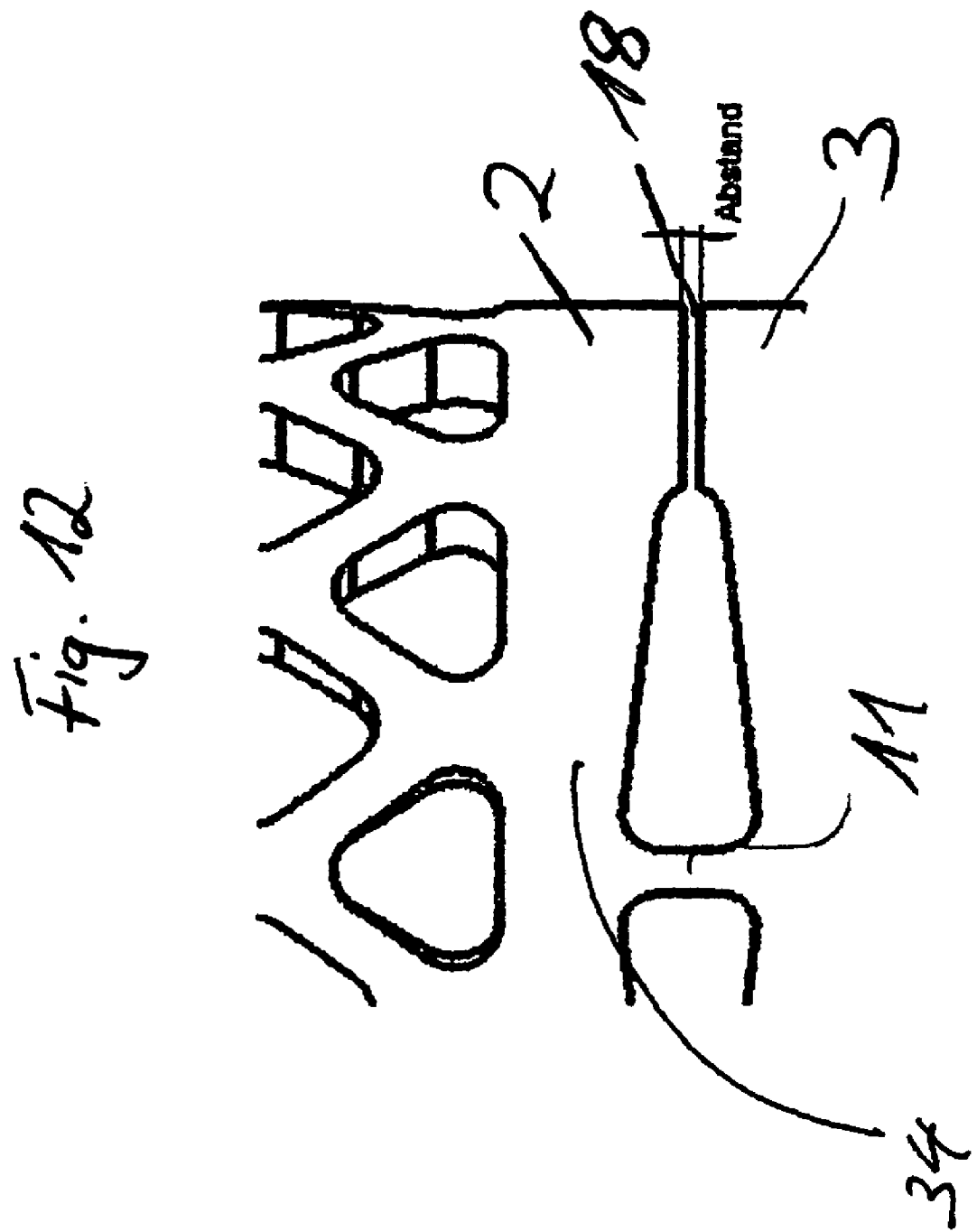

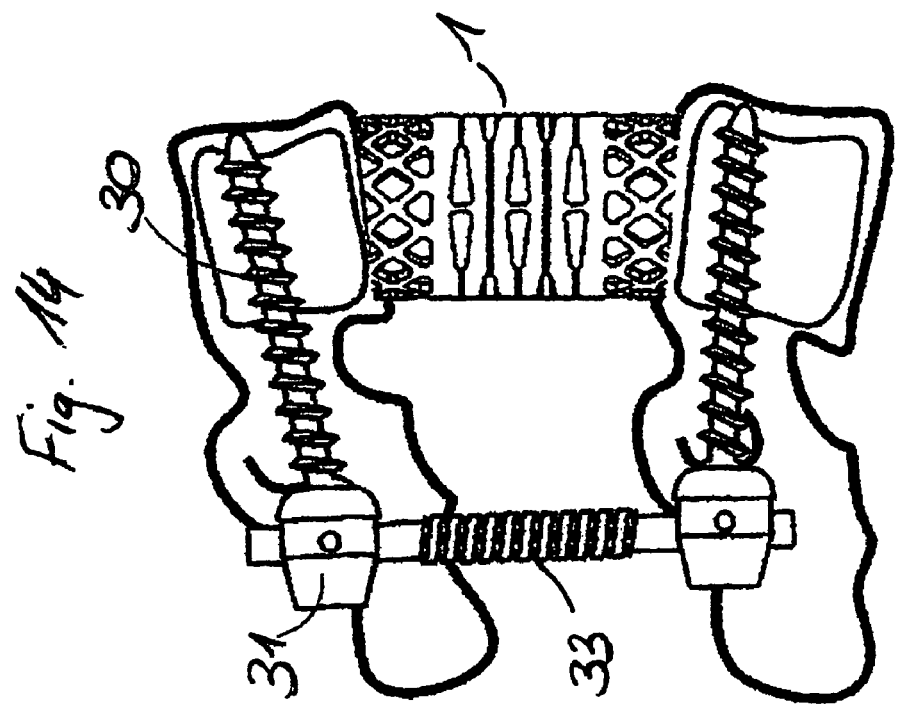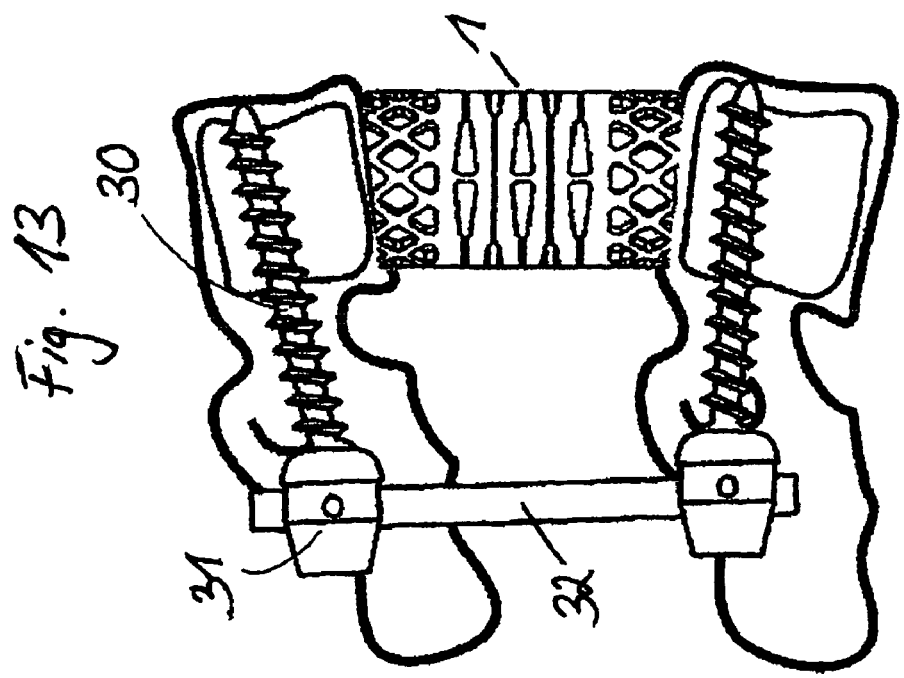

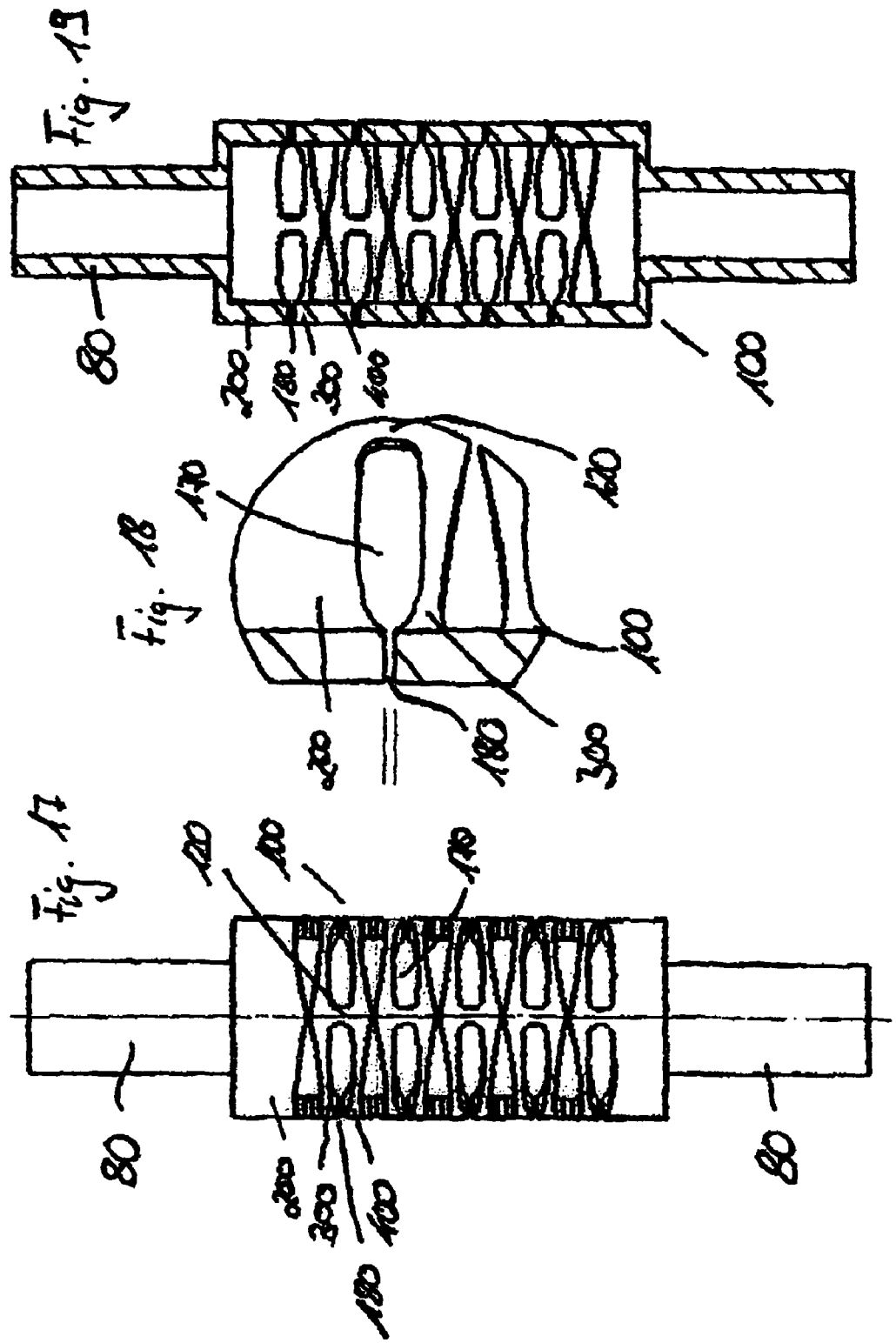

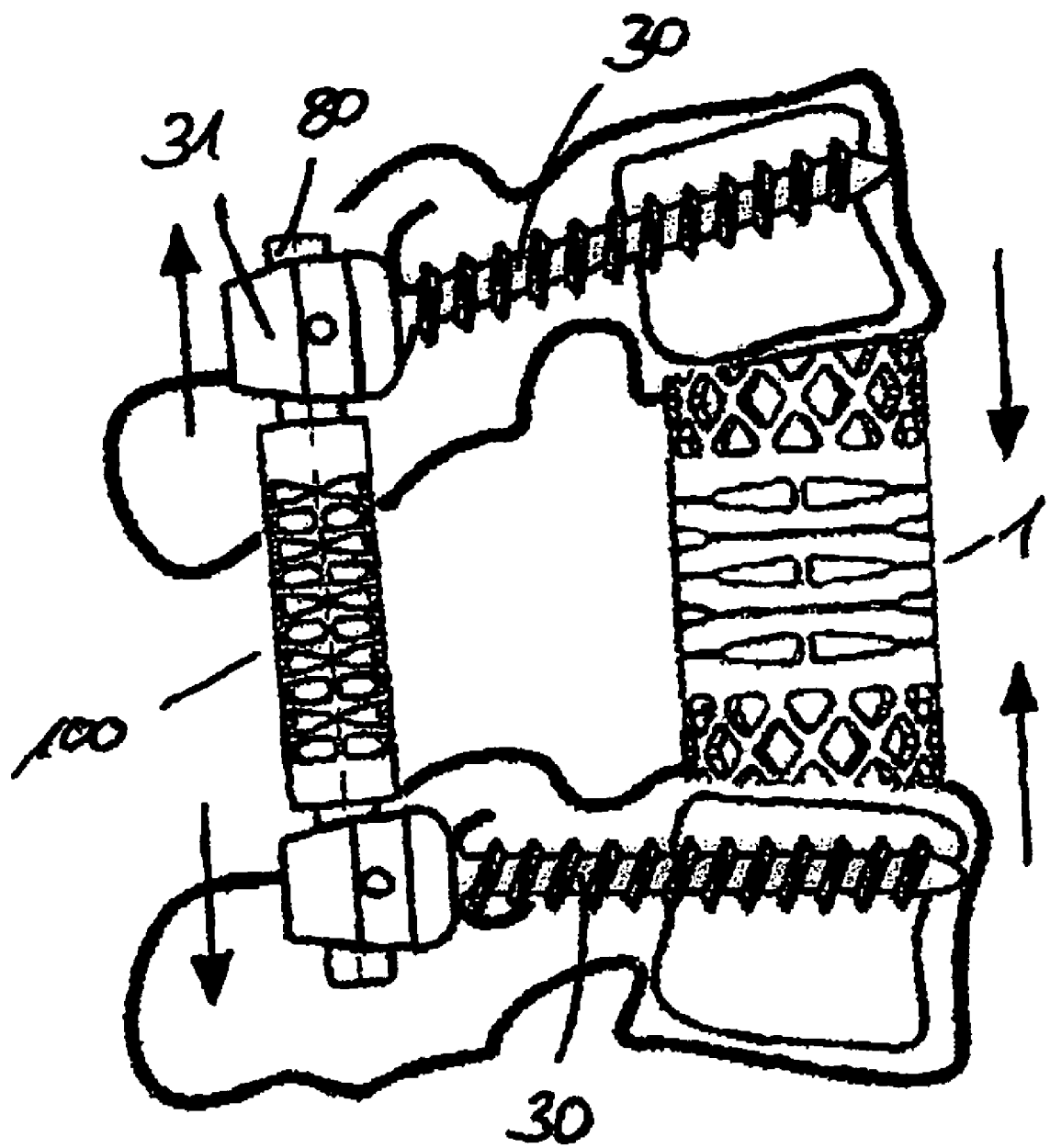

IMPLANT WITH ONE PIECE SWIVEL JOINT

RELATED APPLICATION(S)

The present application claims the benefit of U.S. Provisional Patent Application Ser. No. 60/730,587, filed Oct. 26, 2005, and claims priority from EP 05110043, filed Oct. 26, 2005, the entire disclosures of which are incorporated herein by reference.

BACKGROUND OF THE INVENTION

The present invention relates to an implant for permanent or temporary incorporation into the human or animal body and a placeholder for vertebrae, an intervertebral disc replacement or a connecting rod for pedicle screw arrangements as well as a stabilization system made from these components.

In modern medicine, use of implants to replace parts of the human skeleton following illness, injury or age-related wear-phenomena is widespread. Thus, it is known, for example, in the case of spinal injury such as breaks or when parts of the spinal column are attacked by a tumour, corresponding vertebrae are replaced by placeholders. Such placeholders are described, for example, in European patent EP 0 268 115 B 1.

In a similar manner, intervertebral discs may be replaced by corresponding placeholders, such as described in DE 43 23 034 C1. These placeholders, which generally have a cylindrical tubular base structure, must essentially accommodate axial compressive forces in order to dissipate the forces that are borne by the spinal column. To this end, such placeholders must have adequate strength.

Additionally, a certain amount of flexibility in placeholders may be needed in order to provide movements of the spinal column, especially bending or twisting. For this purpose, prior art placeholders for vertebrae or intervertebral discs provide a combination of the two functionalities, namely strength on the one hand, especially in the axial compressive direction and mobility, and on the other hand, bendability about a rotary axis at right angles to the direction of axial load. Examples of this are DE 103 37 088 A1 and WO 2005/039454 A2. In the case of these placeholders, the central region between the ends, which serve the purpose of arrangement or attachment in adjacent tissue or adjacent vertebrae, has a flexible region, which is achieved either by corresponding elastic materials or by a corresponding structure of the placeholders. WO 2005/039454, for example, discloses a spiral-shaped circumferential slit, which imparts spring-like properties to the base body in the elastic central region.

WO 2005/039454 A2 further discloses that other implants, such as connecting rods for pedicle screw arrangements or similar stabilization systems, may have a certain flexibility derived from corresponding helical shapes, in addition to an ability to transmit forces.

Although these solutions yield very good results with regards the attainable flexibility, deficits concerning the strength and the extent of the axial compressive load that can be accommodated still exist.

Therefore a need for a placeholder that provides opposite functionalities is given. The functionalities comprise primarily flexibility and mobility. In addition, there must be a strength or load bearing capacity. Further, the implant, e.g. the placeholder should be simple to manufacture and should allow easy handling during surgery.

SUMMARY

In accordance with one aspect of the present invention, an implant for permanent or temporary introduction into a human or animal body is provided that includes a base body having a load axis, along which primarily at least one of tensile and compressive forces are transmissible. The implant further includes at least one swivel joint formed in one piece with the base body, the at least one swivel joint has a rotary axis formed transversely to the load axis that facilitates at least limited bending of the base body about the rotary axis. The implant can be used as any one or a combination of a placeholder, an intervertebral disc replacement and a connecting rod for connecting pedicle screws.

Swivel joints are capable of transmitting loads, for example in the axial load direction, and facilitate bending by rotation about a rotary axis that defines the swivel joint. A film hinge can make the noted feature of a one piece swivel joint possible. A film hinge refers to a thin film region or ligament region or generally a wall region that is provided, which, through its dimensional design, facilitates a corresponding elasticity and thus rotational or swivelling motion. This flexibility is achieved by design even though the same rigid material is used.

In accordance with the invention, at least one such swivel joint is provided to facilitate tilting of the ends of the implant or bending thereof in at least in one direction. In accordance with another aspect of the invention, several swivel joints are provided, which are preferably arranged in different planes, especially along the principal load axis, as well as rotated about the principal load axis. Especially, a structure is preferred in which different rotary axes are offset alternating at 90° to each other in different planes, such that bending of the implant in every direction is ensured.

In accordance with another aspect of the invention, an implant is provided having an essentially tubular base body that is built up from several discs or ring elements arranged one on top of the other, which are each connected to each other by correspondingly swivel joints or film hinges, but are otherwise spaced apart from each other, such that room for free movement is present during rotation about the corresponding swivel joint.

The swivel joints may be each arranged along the bisector of the individual ring or disc elements, while a cutout follows on both sides of the film hinge to provide the necessary room for movement.

The cutout between adjacent ring or disc elements, i.e. the spacing between these, can decrease from the swivel joint or film hinge such that there is only a slit-like space at the edging. This slit-like space defines on the one hand the possible tilting of adjacent disc or ring elements towards each other and, in the event of axial compression along the principal load axis of the implant, simultaneously defines the potential mutual contact surfaces, which can serve to dissipate load. Accordingly, in the event of axial compressive loads along the principal load axis, initially the swivel joint or film hinge can accommodate the load. Due to the disc or ring elements being connected to each other via the film hinges with the thickness of the disc or ring elements decreasing in the vicinity of the film hinges on account of the larger cutouts, further increase in axial loading can lead to elastic deformation or especially bending of the disc or ring elements until the slit-like space between the adjacent discs ring elements is completely closed. When the adjacent disc or ring elements in the region of the slit-like cutout are in contact, these edge contact areas also take on the function of load dissipation, such that corresponding strength is present even in the event of very high axial compressive loads. Simultaneously, however, on account of the micro-movement that is ensured by the slit-like cutouts both in the axial direction, e.g. by compression, and for rotation or bending at right angles to the principal load axis, overloading of the neighbouring segments is prevented and rapid on-growth of the end plates of a corresponding placeholder is facilitated, since the placeholder allows small movements, without tearing of the end plates occurring.

Correspondingly, connecting means are provided at the end disc or ring elements, which facilitate engagement with and in-growth into adjacent body parts or attachment of the implant to other implant components. For this purpose, serrations, blunted serrations, recesses, cutouts and the like are provided which are also particularly characterized by the fact that they can be adjusted readily to any desired length on account of their design.

The film hinges are preferably formed such that, starting from the outer circumferential wall of the tubular base body between the adjacent disc or ring elements, inward-running radial ligaments are provided that may additionally be connected to the corresponding disc or ring elements by lateral plate elements. Preferably, the ligaments or film hinges are not of a continuous design, but rather two opposing fillets are provided, which are spaced apart from each other in the central region, such that a continuous opening is created along the central axis, said opening capable of being designed differently in shape and structure, for example, a cloverleaf, a cross, and the like.

The material for the preferably one-piece-manufactured base body, i.e. especially the disc and ring elements or ligaments of the film hinges, may be selected from different materials. Especially, all biocompatible metals, metal alloys and polymers are suitable. Due to the structure of the base body, essentially very rigid materials may also be used, since the flexibility and mobility of the base body are provided by the design. Naturally, materials may also be used that have a certain degree of inherent elasticity and so as to provide certain degree of mobility and flexibility.

BRIEF DESCRIPTION OF THE FIGURES

Further characteristics and features of the present invention are apparent from the following detailed description of embodiments using the enclosed drawings. The drawings show in purely schematic form:

FIG. 1 a perspective view of a placeholder according to a first embodiment of the invention;

FIG. 2 a perspective view of a placeholder according to a second embodiment of the invention;

FIG. 3 a perspective view of a placeholder according to a third embodiment of the invention;

FIG. 4 a side view of the placeholder from FIG. 1;

FIG. 5 a side view of the placeholder from FIG. 1, with the side view of FIG. 5 rotated through 90° relative to that of FIG. 4;

FIG. 6 a side view of the placeholder from FIG. 3;

FIG. 7 a side view of the placeholder from FIG. 3, with the side view of the placeholder from FIG. 7 rotated through 90° relative to that of FIG. 6;

FIG. 8 a plan view of the placeholder from FIG. 3;

FIG. 9 a plan view of the placeholder from FIG. 1;

FIGS. 10(a)-(c) are side views of a part of the placeholders of FIGS. 1-3 in different load levels under axial compression;

FIGS. 11(a)-(c) are side views of a part of the placeholders of FIGS. 1-3 in different load levels under bending;

FIG. 12 a detailed view of the placeholder from FIG. 1;

FIG. 13 a schematic side representation of the placeholder from FIG. 1 interacting with a pedicle screw arrangement;

FIG. 14 a schematic side representation of the interaction of the placeholder from FIG. 1 with another type of a pedicle screw arrangement;

FIG. 17 a schematic side representation of a connecting rod according to the invention;

FIG. 18 a detailed cross-sectional view of the connecting rod from FIG. 17;

FIG. 19 a cross-sectional view of the connecting rod from FIG. 17;

FIG. 21 a schematic side representation of the placeholder from FIG. 1 and of the connecting rod from FIG. 20 in operative.

DETAILED DESCRIPTION

Figure 16:
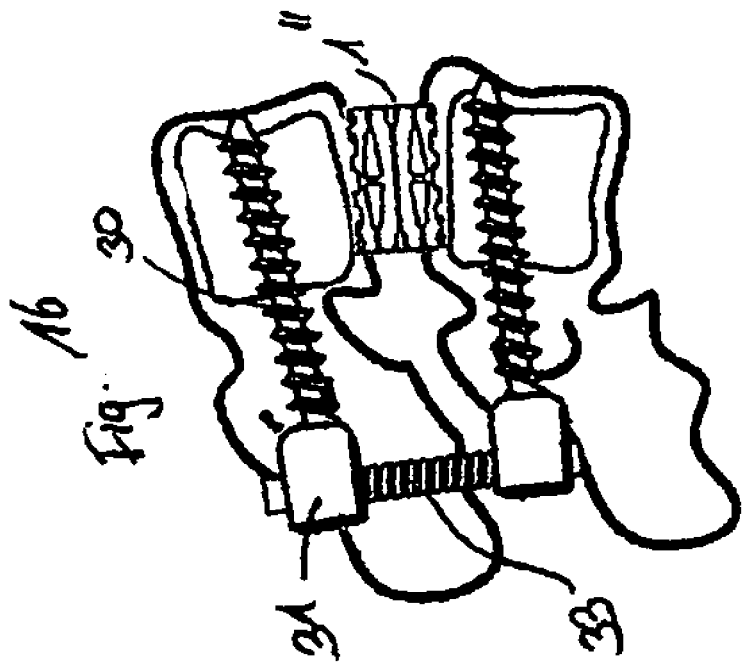
FIG. 16 a schematic side representation of the placeholder from FIG. 3 operatively interacting with a pedicle screw arrangement.

FIG. 1 is a perspective view of a first embodiment of an implant of the invention in the form of a placeholder for a spinal column.

The placeholder 1 has a generally cylindrical tubular base body, which is subdivided into six discs or ring elements 2 to 7 (referred to herein as ring elements), which are arranged on top of each other along the longitudinal axis L, which is simultaneously the primary load axis L. On the outwardly projecting ends of the two end ring elements 2 and 7 are connecting elements 8 to 10, which are formed from blunted serrations 8, diamond-like cut outs or triangular cutouts 9 and triangular recesses 10 between the blunted serrations 8. These connecting elements 8 to 10 serve to engage and grow together with adjacent tissue, cartilage or vertebrae. With the connecting elements 8 to 10, a secure arrangement of the placeholder 1 in the spinal column is ensured.

Between each of the disc or ring elements 2 to 7 are provided two ligaments extending radially from the outside to the inside, said ligaments forming the film hinges 11 to 15. The ligaments forming the film hinges 11 to 15 do not extend completely as far as the central axis, which is parallel to or identical with the load axis L, but rather are spaced apart from each other in the interior region, such that a continuous longitudinal opening is provided between the ligaments, as will be explained in the following. Alternatively, the ligaments may also be restricted to a width corresponding to the wall thickness of the base body or of the disc or ring elements 2 to 7.

Additionally, the film hinges are rotated alternating through 90°, such that the film hinge 11 is arranged at a right angle to the film hinge 12, while this in turn is arranged at right angle to the film hinge 13, etc.

The discs or ring elements 2 to 7 are each connected to one another only by the corresponding film hinges 11 to 15, which separate two semicircular cutouts 17, 18 between the corresponding discs or ring elements 2 to 7 from each other. In the region of the film hinges 11 to 15, the corresponding cutouts 17, 18 have a greater thickness in the direction of the principal load axis L than in regions farther away from the film hinges 11 to 15. Especially, the cutouts 17, 18 between the disc or ring elements 2 to 7 are divided into two parts, with the cross-section of the first part forming 17 a triangular cutout, which, starting from the fillets of the film hinges 11 to 15 having a large thickness, decreases in thickness in the direction of the principal load with increase in distance from the film hinges 11 to 15, and ultimately finishes as a thin slit forming the second part 18 between the disc or ring elements 2 to 7. The essentially triangular cross-sectional shape of the cutout 17 is optimised by rounded edges such that no stress peaks may occur.

The provision of the cutouts 17, 18 on both sides of the film hinges 11 to 15 facilitates tilting of the placeholder 1 through a rotary axis parallel to the ligaments of the film hinges 11 to 15, as indicated by the rotary axes D and the corresponding rotary arrows.

The 90° offset arrangement of the film hinges 11, 13 and 15 to the film hinges 12 and 14 allows the placeholder 1 to bend in every direction about the longitudinal axis L, with saggital tilting angles of up to 5° being achieved.

Two further embodiments of a placeholder 1' and 1" are shown in perspective views of FIGS. 2 and 3, with identical components given the same numerals.

Along the longitudinal axis L of placeholder 1', where primarily tensile and compressive forces are accommodated, placeholder 1' has four disc or ring elements 2', 3', 4', and 5'. These are connected to each other via swivel joints or film hinges 11, 12 and 13, with each of these forming rotary axes D at right angles to the load axis L.

Adjacent to the film hinges 11, 12 and 13, generally triangular cutouts 17 are provided on both sides of the ligaments of the film hinges 11 to 13, said cutouts tapering with increasing distance from film hinges 11 to 13 and finishing as thin slits 18.

At the ends of the placeholder 1' in the direction of the load axis L, namely at disc or ring elements 2' and 5', connecting elements for connection to adjacent vertebrae, cartilage or tissue are provided, with, exactly as in the embodiment of FIG. 1, blunted serrations 8 and triangular cutouts 10 provided. Additionally, only triangular cutouts 9' are present, because the crown at connecting elements of the placeholder 1' is formed much lower than that of placeholder 1.

A further reduction of the crown at connecting elements is to be observed in placeholder 1", which is shown in FIG. 3. Here, no cutouts at all are provided, but rather just blunted tips 8" and trapezoidal recesses 10".

In the embodiment shown in FIG. 3, four disc or ring elements 2", 3", 4" and 5" are connected to each other via alternating film hinges 11, 12 and 13 arranged at right angles to each other, whereas, between the ring elements 2", 3", and 5", corresponding cutouts are present, which affect a spaced arrangement of the ring elements 2", 3", 4" and 5" in the regions outside the film hinges. The distance between the adjacent ring elements 2", 3", 4" and 5" is much greater in the region of the cutout 17 of triangular cross-section than in the region of the slit formation 18, with, as in the other embodiments, approximately half of the circumference of each ring element being provided in the region of the slit space, while the other half of the circumference has a much greater space between the ring elements 2" to 5". Each ring element 2", 3", 4" and 5" also includes a rib that extends toward the center of the corresponding ring element from the inner wall of the ring element. In FIG. 3, the ring element 2" is shown to have ribs 11" (also shown in FIG. 8) that are arranged at right angles to the film hinges 11. Accordingly, the ribs 11" are positioned above and separate from the film hinges 12 of the ring element 3". Similarly, the ring element 2' of FIG. 2 includes two ribs 11' that extend from the wall of the ring element 2' toward the center and are arranged at right angles to the film hinges 11. Accordingly, the ribs 11' are positioned above and separate from the film hinges 12 of the ring element 3'.

FIGS. 4 to 7 illustrate placeholders 1 and 1". FIGS. 4 and 5 show two side views of the placeholder 1, which are rotated at 90° to each other about the axis L. FIGS. 4 and 5 show that the film hinges 11, 13 and 15 on the one hand and the film hinges 12 and 14 on the other hand as well as the corresponding pertinent rotary axes D are rotated through 90° to each other, with slits 18 facilitating tilting about the respective rotary axes D between the corresponding ring elements 2 to 7.

FIGS. 6 and 7 similarly show the placeholder 1" with a reduced number of disc or ring elements as well as film hinges 11 to 13 and rotary axes D.

FIGS. 8 and 9 show plan views of the placeholders 1" (FIG. 8) and 1 (FIG. 9). These plan views show that both the placeholder 1" and the placeholder 1 generally have a cylindrical tubular body, which is built up from the corresponding ring or disc elements. The plan views also show that the film hinges, such as the film hinges 11 and 12 of the placeholder 1" in FIG. 8, are formed by inwardly running radial ligaments, which are spaced apart from each other in the middle of the placeholder, such that a central opening 19 is formed there by the overall placeholder 1" along the load axis L.

Because as the ligaments of the film hinges 11 to 15 are attached only via the outer wall of the connected ring or disc elements, further cavities 20 to 23 are formed between the corresponding ligaments of the film hinges 11 to 15, said cavities also being continuous and parallel to the load axis, such that a cloverleaf-shaped cavity 19 to 23 is formed extending through placeholder 1".

The ligaments are stabilized by the portion of the ligaments that extend radially inward from the outer wall of the disc or ring elements. Alternatively, the ligaments forming the film hinges 11 and 15 may however also be stabilized laterally by corresponding plates 16 (see FIG. 1) or attached at the corresponding ring or disc elements 2 to 7. If such plates 16, as in the embodiment of FIG. 1, are triangular, the overall plan view is a continuous cross-like cavity 24, with the ligaments that form the film hinges 11 to 15 arranged in the region of the dashed lines 25 of FIG. 9.

FIGS. 10 and 11 show the operation of the placeholders 1, 1' and 1".

As is shown in FIGS. 10(a)-10(c), the film hinges, for example film hinge 12 or the corresponding ligaments, are elastically compressed on application of the axial compressive force along the primary load axis L. Additionally primarily the discs or rings 3, 4 may be elastically deformed or bent in the region of their weakest formation, i.e. in the vicinity of the ligament 12, until the spaced disc elements 3 and 4 make contact with each other in the region of slit formation 18. As shown in FIG. 10(b), the axial load is accommodated not only by the ligaments of the film hinge 12, but is also accommodated by the edge areas of the disc elements 3 and 4 lying one on top of the other. Accordingly, a larger axial load may be accommodated. If, as shown in FIG. 10(c), the axial load, i.e. compressive force, is increased further, the disc elements 3 and 4 in the region of the slit formation 18 are pressed further together and thus take on the principal load, because the contact surface is now much larger than the cross-sectional surface of the ligaments of the film hinge 12.

In the case of a bending load, as illustrated in FIG. 11, the thinly formed ligaments of the film hinge 12 facilitate rotation about the axis perpendicular to the plane of the figure. Accordingly, one-sided contact of the edge surfaces of the disc or ring elements 3 and 4 occurs in the region of the slit formation 18 and corresponding bending of the placeholder or tilting of the ends of the placeholder towards each other. After this limited tilting or bending possibility, contact of the disc elements 3 and 4 with each other in the region of the slit formation (see FIG. 11 (b)) of FIG. 11) leads to load accommodation in the region of the slit formation 18, such that further tilting is prevented and additionally, with increasing application of load, stabilization occurs through a correspondingly larger contact region (see FIG. 11(c)) of FIG. 11).

As shown from FIGS. 10 and 11, the shape of the cutouts 17 and 18 between the disc or ring elements 3 and 4 facilitates adjustment of the possible tilting or bending region and as well as the stability and strength of the overall implant. If the proportion of the slit region is enlarged overall, greater strength is the result, because greater contact surface area is present. If the slit thickness, i.e. the space between the discs, is enlarged, the bendability is increased.

FIG. 12 illustrates once again in detail the effect of the slit region between the disc or ring elements 2 and 3. The space, which is defined by the slit 18 between the disc or ring elements 2 and 3, determines the degree of mobility or tilting between the disc or ring elements 2 and 3. The greater the space, the greater is the rotational ability of the disc or ring elements 2 and 3 relative to the film hinge 11. Furthermore, the size of the possible contact surface in the slit region 18 determines the size of the transmissible load in the case of axial compression or corresponding bending. The formation of the disc or ring elements 2 and 3 in the region 34 determines the bendability of the disc or ring elements 2 and 3 and thus the elasticity in the direction of the load axis L.

FIGS. 13 to 16 show different applications of implants of the invention. FIG. 13 shows the placeholder 1 in combination with a pedicle screw arrangement, with the pedicle screws 30 in the adjacent vertebrae being connected at their screw heads 31 by a connecting rod 32 and exerting a stabilizing function. In this embodiment, the connecting rod 32 is formed semi-rigidly via the elasticity implied by the material.

FIG. 14 shows the placeholder 1 in a similar application, with just the semi-rigid connecting rod 32 in the pedicle screw arrangement replaced by a flexible connecting rod 33, which in this case derives its flexibility from a helical-screw-like design with a core element. Alternatively, a connecting rod having the invention's structure of discs, connected by swivel joints, could be used for the connecting rod 33.

Figure 15:
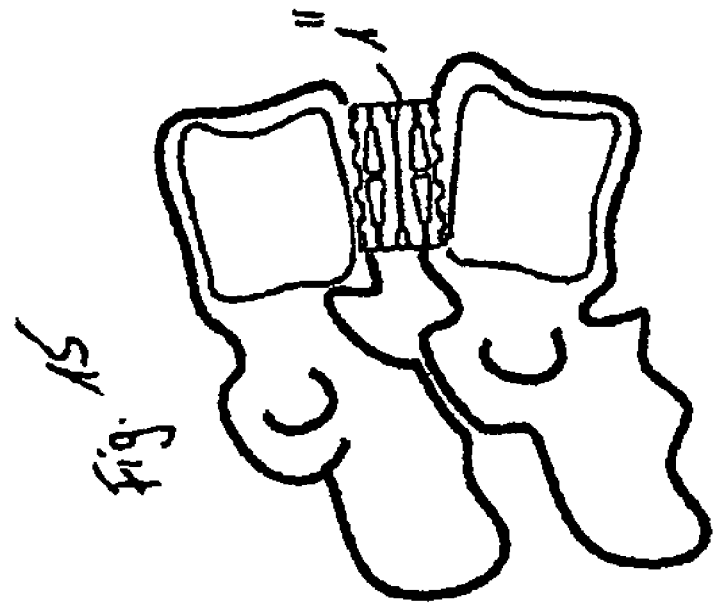
FIG. 15 a schematic side view of the placeholder from FIG. 3 shown operating between two vertebrae.

FIGS. 15 and 16 show the application of the placeholder 1" without a stabilization device and with a stabilization device, respectively. On account of the lower installed height of the placeholder 11", the placeholder is used here as an intervertebral disc replacement, with a stabilizing pedicle screw arrangement of pedicle screws 30 and an elastic connecting rod 33 being provided.

FIG. 17 shows a flexible connecting rod 100, which in a central region, comprises a base body structure of the invention corresponding to placeholder 1 having articulated disc or ring elements 200, 300, 400, connected by swivel joints, with the joints being offset at 90° to each other in alternating fashion.

The joints are formed by film hinges 120, which, for example, are formed by corresponding connecting ligament between the disc or ring elements 200, 300, 400, with the width of the ligaments 120 corresponding to the wall thickness of the disc or ring elements 200, 300, 400.

At the axial ends of the connecting rod 100 connecting pieces 80 are provided for accommodation of screw heads of pedicle screws, for example. In the embodiment shown in FIG. 17, the connecting pieces 80 have a smaller cross-section than the central region. However, rods having an continuously invariable cross-section are also conceivable.

FIG. 18 shows in a detailed view of the connecting rod 100 from FIG. 17 that here the corresponding disc or ring elements 200 and 300 are connected to each other only by corresponding ligaments 120, whereas a bottle-shaped cutout 170, 180 with a broad cutout region 170 and a slit-like cutout region 180 is provided between the disc or ring elements 200, 300 in the other wall region. The shape of the cutouts 170, 180 and especially the thickness of the slit 180, in turn defines the compressibility and the tilting or bendability of the connecting rod 100.

FIG. 19 shows a cross-sectional view of the connecting rod 100 of FIG. 17. As shown, the connecting pieces 80 are formed in one-piece with the base body. However, it is also possible to detachably connect the connecting pieces 80 to the base structure in a suitable manner, for example with corresponding screw connections.

Figure 20:
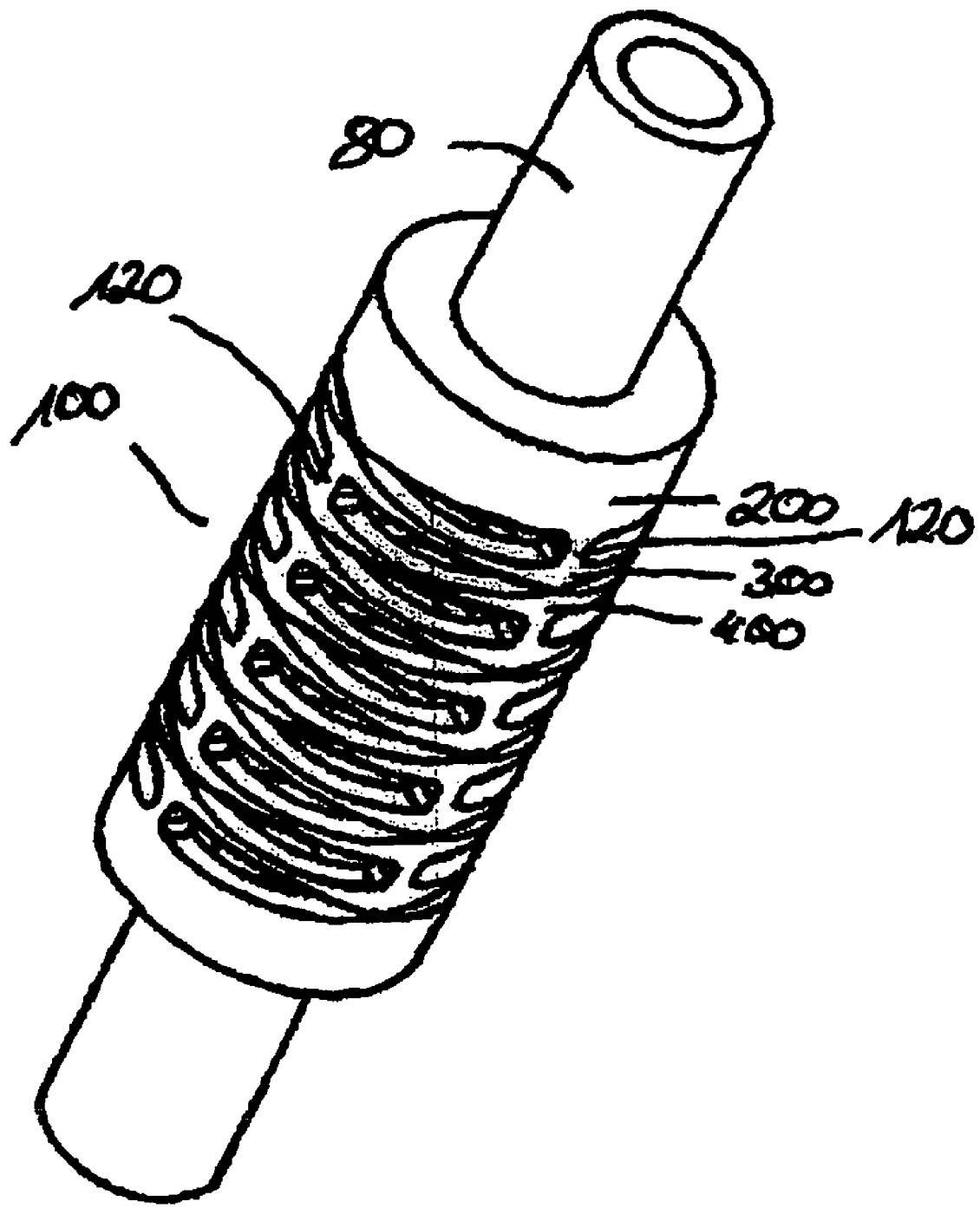
FIG. 20 a perspective view of the connecting rod from FIG. 17.

FIG. 20 shows the flexible connecting rod 100 in a perspective view which shows that the cylindrical tubular base structure is built up from ring elements 200, 300, 400 connected in articulation by ligaments or film hinges 120, with the ligaments or the film hinges of adjacent ring elements each rotated through 90° relative to each other.

FIG. 21 shows an application of the placeholder 1 of the invention and of the flexible connecting rod 100 as well as a stabilization system with pedicle screw arrangement. The pedicle screws 30 screwed into the vertebrae are connected to each other via the flexible connecting rod 100, with the connecting pieces 80 being accommodated by the screw heads 31. The placeholder 1 is provided between the vertebrae. By means of both the flexible formation of the placeholder 1 and the connecting rod 100, it is, for example, possible, as indicated by the arrows in FIG. 21, to compress the placeholder 1 and simultaneously extend the flexible connecting rod 100 and vice versa. Additionally, both the flexible connecting rod 100 and the flexible placeholder 1 can execute corresponding bending or tipping of their axial ends. Accordingly, the requirements for strength on the one hand and flexibility on the other hand may be fulfilled.

What is claimed is:

1. An implant for permanent or temporary introduction into a human or animal body, the implant comprising:
    a base body having an outer wall surface and an inner wall surface, the base body further having a load axis along which primarily at least one of tensile and compressive forces are transmissible; and
    at least one swivel joint formed in one piece with the base body, the at least one swivel joint having a rotary axis formed transversely to the load axis, said rotary axis facilitating at least limited bending of the base body about the rotary axis;
    wherein the base body comprises a first ring or disc element and a second ring or disc element and wherein the at least one swivel joint comprises first and second ligaments connecting the first ring or disc element to the second ring or disk element, each of the first and second ligaments extends radially inward from the outer wall surface toward a central axis of the base body parallel to the load axis and beyond the inner wall surface of the base body;
    wherein the first ring or disc element is spaced apart from the second ring or disc element along the central axis of the base body by the first and second ligaments, forming cutouts between the ligaments.

2. An implant in accordance with claim 1, further comprising more than two ring or disc elements and several swivel joints with their rotary axes in different planes arranged transversely to the load axis.

3. An implant in accordance with claim 1, further comprising more than two ring or disc elements and several swivel joints with rotary axes mutually rotated about the load axis.

4. An implant in accordance with claim 1, further comprising more than two ring or disc elements and several swivel joints along the load axis in several planes lying one on top of the other, wherein the swivel joints are offset from each other by 90°.

5. An implant in accordance with claim 1, wherein each of the first and second ligaments is a film hinge, the thickness of the firm hinge, measured in a circumferential direction around the central axis of the base body, is less than the greatest height of the cutout, measured in the direction of the central axis of the base body.

6. An implant in accordance with claim 1, wherein the two ligaments are formed opposite each other along the rotary axis.

7. An implant in accordance with claim 6, wherein the cutouts are arranged in a plane at a right angle to the load axis, and wherein the swivel joint is provided at a right angle to the plane of the cutouts, wherein the cutouts are arranged on both sides of the swivel joint such that tilting about the swivel joint is enabled.

8. An implant in accordance with claim 7, wherein each cutout tapers from the corresponding swivel joint at least in a wall region of the base body.

9. An implant in accordance with claim 1, wherein the swivel joint is arranged along a bisector of the base body.

10. An implant in accordance with claim 1, wherein the base body has more than two disc or ring elements and several swivel joints, each disc or ring element connected to another disc or ring element by a respective swivel joint.

11. An implant in accordance with claim 10, wherein the more than two disc or ring elements have a continuous opening arranged centrally and coaxially to the central axis along the load axis.

12. An implant in accordance with claim 11, wherein the opening is any one of star-shaped, cross-shaped and cloverleaf-shaped.

13. An implant in accordance with claim 10, wherein the base body has an odd number of swivel joints and an even number of disc or ring elements.

14. An implant in accordance with claim 10, wherein the disc or ring elements are elastically deformable along the load axis.

15. An implant in accordance with claim 10, wherein the disc or ring elements are elastically deformable along the load axis in the vicinity of the swivel joints.

16. An implant in accordance with claim 1, wherein the base body is elastically deformable parallel to the load axis in the axial direction.

17. An implant in accordance with claim 1, wherein the base body is formed as a tubular body with a cylindrical cross-sectional shape.

18. An implant in accordance with claim 1, wherein the base body has a connecting element at each end, each connecting element formed by a plurality of projections arranged along the load axis.

19. An implant in accordance with claim 1, wherein the base body has a connecting element at each end, each connecting element formed by a plurality of cutouts into the inner and outer wall surfaces of the base body.

20. An implant in accordance with claim 1 in the shape of a connecting rod to connect to pedicle screws having screw connections,
  wherein the base body has connecting elements at its ends arranged along the load axis, and wherein the connecting elements are configured to be attachable to the screw connections.

21. An implant in accordance with claim 1, further comprising lateral plate elements extending from each side of the first and second ligaments to the inner wall of the base body.

22. An implant for permanent or temporary introduction into a human or animal body, the implant comprising:
  a base body having a load axis along which primarily at least one of tensile and compressive forces are transmissible; and
  at least one swivel joint formed in one piece with the base body, the at least one swivel joint having a rotary axis formed transversely to the load axis, said rotary axis facilitating at least limited bending of the base body about the rotary axis;
  wherein the base body comprises a first ring or disc element and a second ring or disc element and wherein the at least one swivel joint comprises first and second ligaments connecting the first ring or disc element to the second ring or disk element, each of the first and second ligaments extends radially inward from an outer wall surface toward a central axis of the base body parallel to the load axis;
  wherein the first ring or disc element is spaced apart from the second ring or disc element along the central axis of the base body by the first and second ligaments, foaming cutouts between the ligaments;
  wherein each of the first and second ligaments is a film hinge, the thickness of the film hinge, measured in a circumferential direction around the central axis of the base body, is less than the greatest height of the cutout, measured in the direction of the central axis of the base body.

23. An implant in accordance with claim 22, wherein the base body has more than two disc or ring elements and several swivel joints, each disc or ring element connected to another disc or ring element by a respective swivel joint.

24. An implant in accordance with claim 23, wherein the more than two disc or ring elements have a continuous opening arranged centrally and coaxially to the central axis along the load axis.

25. An implant in accordance with claim 22, wherein the base body has a connecting element at each end, each connecting element formed by a plurality of projections arranged along the load axis.

* * * * *

UNITED STATES PATENT AND TRADEMARK OFFICE
CERTIFICATE OF CORRECTION

| | | |
|---|---|---|
| PATENT NO. | : 8,152,849 B2 | Page 1 of 1 |
| APPLICATION NO. | : 11/588687 | |
| DATED | : April 10, 2012 | |
| INVENTOR(S) | : Lutz Biedermann | |

It is certified that error appears in the above-identified patent and that said Letters Patent is hereby corrected as shown below:

In the Specification

Column 7, line 41.          Delete "11","
                            Insert -- 1", --

In the Claims

Column 10, Claim 22, line 33.    Delete "foaming"
                                 Insert -- forming --

Signed and Sealed this
Thirtieth Day of October, 2012

David J. Kappos
*Director of the United States Patent and Trademark Office*